United States Patent
Germann et al.

(12)

(10) Patent No.: US 6,306,879 B1
(45) Date of Patent: Oct. 23, 2001

(54) STABLE AQUEOUS SOLUTION OF 3-(1-OXO-1,3-DIHYDROISOINDOL-2-YL)-PIPERIDINE-2-6-DIONE

(75) Inventors: Tieno Germann, Herzogenrath; Heinrich Kugelmann, Aachen, both of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/540,203

(22) Filed: Mar. 31, 2000

(30) Foreign Application Priority Data

Mar. 31, 1999 (DE) ............................................. 199 14 621

(51) Int. Cl.$^7$ ................................................. A61K 31/445
(52) U.S. Cl. ............................................................... 514/323
(58) Field of Search ............................................. 514/323

(56) References Cited

FOREIGN PATENT DOCUMENTS

| 42 11 812 | 10/1992 | (DE) . |
| 196 13 976 | 11/1997 | (DE) . |
| 0 908 176 | 4/1999 | (EP) . |
| 197 43 968 | 4/1999 | (DE) . |
| WO 94/20085 | 9/1994 | (WO) . |
| WO 94/20085 A1 | * 9/1994 | (WO) . |

OTHER PUBLICATIONS

Koch et al., "Löslichkeits—und Stabilitätsverbesserung von Thalidomid durch Bildung von Einschlußkomplexen mit Cyclodextrinen", *Arch. Pharm.* 321., pp. 371–373 (1988).

Trinchieri, "Interleukin–12: A Proinflammatory Cytokine with Immunoregulatory Functions that Bridge Innate Resistance and Antigen–Specfic Adaptive Immunity", Annu. Rev. Immunol. 1993, 13, pp. 251–276.

Schmahl et al., "The Enantiomers of the Teratogenic Thalidomide Analogue EM 12", Toxicology Letters, 45 (1989), pp. 23–33.

* cited by examiner

*Primary Examiner*—Dwayne C. Jones
(74) *Attorney, Agent, or Firm*—Crowell & Moring LLP

(57) ABSTRACT

An aqueous solution 3-(1-oxo-1,3-dihydroisoindol-2-yl)-piperidine-2,6-dione (EM 12) is described which is suitable for parenteral administration, particularly for intravenous administration of EM 12 for treating immunological and haematological-oncological diseases, and a method of producing the corresponding solution of EM 12 is also described.

4 Claims, No Drawings

STABLE AQUEOUS SOLUTION OF 3-(1-OXO-1,3-DIHYDROISOINDOL-2-YL)-PIPERIDINE-2-6-DIONE

BACKGROUND OF THE INVENTION

This invention relates to a parenteral form of administration of the thalidomide derivative 3-(1-oxo-1,3-dihydroisoindol-2-yl)-piperidine-2,6-dione (EM 12) and to a method for its production. This form of administration can be used for the therapy of inflammatory and haematological-oncological diseases.

The excess formation of the proinflammatory cytokine TNF-α (tumour necrosis factor) and of interleukin (IL)-12 by phagocyte cells (e.g. monocytes) plays a central part in the pathogenesis of various inflammatory diseases (Trinchieri 1995, Ann. Rev. Immunol. 13: 251).

One approach to the treatment of these diseases is to deliberately suppress the formation of these proinflammatory cytokines by the administration of immunomodulating active ingredients, such as dexamethasone or thalidomide, or the thalidomide derivative EM 12, for example. Whereas corticoids such as dexamethasone exist in injectable forms, this has not hitherto been the case for the derivative EM 12, which has an inmmunomodulatory effect. A parenteral form of administration for thalidomide has been proposed in co-pending U.S. Pat. No. 6,124,322, the disclosure of which is incorporated herein by reference.

Thalidomide has proved to be superior to classical immunosuppressants for the treatment of severe aphthous stomatitis. Other examples of diseases in which thalidomide has been shown to exhibit good efficacy without resulting in general immunosuppression include cutaneous lupus erythematodes, pyoderma gangrenosum and urogenital ulcers in Bechet's syndrome, as well as ulcerations, in those infected with HIV, which do not differ histologically from aphthous ulcers and in which—as distinct from most HIV-associated mucocutaneous lesions—no microbial causative agents can be detected. As distinct from aphthous stomatitis, these lesions, which can also sometimes assume the size of major aphthae, can occur in the entire digestive tract, and when they are located in the pharyngeal cavity or the gullet they can make the ingestion of food difficult and can also make the ingestion of oral medication difficult due to the pain which they cause.

In severe cases of pharyngeal or oesophageal ulcers in which oral ingestion is made difficult or may even be impossible, and in cases of HIV-associated pathology in which severe symptoms of diaorrhea make oral ingestion unpredictable, parenteral administration provides a solution. However, the low solubility in water of thalidomide (Arch. Pharm. 321, 371 (1988)) constitutes an obstacle to the parenteral administration of this active ingredient. There has therefore been no lack of attempts aimed at the development of water-soluble forms of administration.

Water-soluble thalidomide derivatives, which exhibit a considerably higher solubility in water than that of thalidomide and which are suitable for parenteral administration, are known from DE 42 11 812.

Furthermore, thalidomide prodrugs have been proposed for parenteral administration which can be administered in water-soluble form within the physiological pH range and are toxicologically harmless (DE 196 13 976). It is disadvantageous that the production of both types of compounds mentioned above is more costly than the production of thalidomide.

The thalidomide derivative EM 12 exhibits similar disadvantageous properties to thalidomide as regards its solubility in an aqueous medium and its tendency to undergo spontaneous hydrolysis. It has been found that the production of aqueous solutions is not practicable, due to the tendency of EM 12 to undergo spontaneous hydrolysis.

SUMMARY OF THE INVENTION

An object of the invention was to provide a water-soluble form of administration for the thalidomide derivative EM 12, which has an immunomodulatory effect.

A further object of the invention was to provide a form of administration which would be stable in its aqueous dissolved form, and which would have no physiologically incompatible physicochemical properties which would result in toxicological effects.

In accordance with the present invention, these and other objects have been achieved by providing a stable aqueous solution containing EM 12 for parenteral administration, wherein the EM 12 is dissolved in an isotonic glucose solution and the pH of the solution is less than or equal to 5.5.

It has been found that if the pH of an aqueous EM 12 solution falls within a range of pH which is less than or equal to 5.5, spontaneous hydrolysis of EM 12 does not occur.

TABLE 1

Structure of the substances thalidomide and EM 12

| Substance | Structure | Name |
|---|---|---|
| Thalidomide | 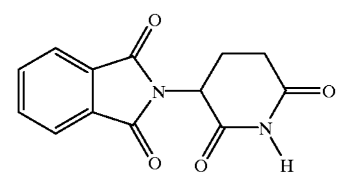 | 2-(2,6-dioxo-piperidin-3-yl)-isoindole-1,3-dione |
| EM 12 | 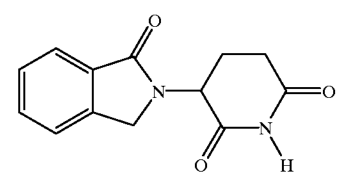 | 3-(1-oxo-1,3-dihydro-isoindol-2-yl)-piperidine-2,6-dione |

Accordingly, the present invention relates to a solution of EM 12 which is suitable for parenteral administration, wherein said solution is an aqueous solution with a pH less than or equal to 5.5 and contains glucose as a constituent. According to the invention, EM 12 is dissolved, either as a racemate or in the form of one of its enantiomers, in an isotonic glucose solution. Solutions of this type can be used for parenteral administration, particularly for intravenous administration.

Forms of administration of EM 12 which have an active ingredient content of at least 0.2 mg/ml are suitable as injectable forms of administration.

The present invention further relates to a method of producing said aqueous solution. According to this aspect of the invention, EM 12 is added to an isotonic glucose solution with a pH of 4 to 5 and this mixture is shaken until dissolution of the EM 12 is complete and/or is subsequently treated with ultrasound in order to shorten the time of production, and is filtered under aseptic conditions.

The form of administration according to the invention is toxicologically harmless, both when administered as a rapid infusion and when administered as a slow infusion (10 ml/min).

Apart from EM 12, the pharmaceutical compositions according to the invention also contain glucose. Other adjuvant substances can also optionally be added to the EM 12 solution. The choice of such further adjuvant substances and the amounts thereof which are used depend on how the drug is to be administered.

The amount of active ingredient to be administered to the patient, which depends on the weight of the patient, on the indication and on the degree of severity of the disease, usually ranges between 0.1 and 1 mg/kg.

Parenteral EM 12 solutions can be used, as can thalidomide solutions also, for the therapy of diseases in which an excess production of TNF-α and JL-12 is responsible for pathogenesis (including, amongst others, diseases of the bowels, of the skin, of the mucous membranes and of the vessels, as well as autoimmune diseases). Furthermore, due to their anti-angiogenetic effect, they can also be used for the therapy of haematological diseases and other oncological diseases.

The diseases of the aforementioned groups include, amongst others, inflammations of the skin (e.g. atopical dermatitis, psoriasis, eczema), inflammations of the respiratory tracts (e.g. bronchitis, pneumonia, bronchial asthma, ARDS (adult respiratory distress syndrome), sarcoidosis, silicosis/fibrosis), inflammations of the gastrointestinal tract (e.g. gastroduodenal ulcers, Crohn's disease, ulcerative colitis), and also include diseases such as hepatitis, pancreatitis, appendicitis, peritonitis, nephritis, aphthosis, conjunctivitis, keratitis, uveitis, rhinitis.

Autoimmune diseases comprise, for example, diseases of the arthritic type (e.g. rheumatoid arthritis, diseases associated with HLA-B27), and also include multiple sclerosis, juvenile diabetes and lupus erythematosus.

Further indications include sepsis, bacterial meningitis, cachexia, transplant rejection reactions and graft-versus-host reactions, as well as reperfusion syndrome and atherosclerosis.

Other diseases which can be treated include haematological diseases such as multiple myeloma and leukemia, as well as other oncological diseases such as glioblastoma, cancer of the prostate and breast cancer.

EXAMPLE

In order to produce an infusion solution in a concentration of 200 μg/ml, 70 mg of racemic EM 12 in 350 ml of a 5% glucose solution for infusions (pH 4 to 5) were introduced into a glass infusion bottle. The mixture was thoroughly shaken and was treated with ultrasound for 15 minutes. Since the concentration of dissolved EM 12 depended upon the intensity of shaking and on the ultrasonic treatment, both steps were repeated until complete dissolution was achieved. The water temperature in the ultrasonic bath reached a maximum of 33° C. The solution was filtered under aseptic conditions through a Millex GS sterile filter with a pore size of 0.22 μm (Millipore S. A., Molsheim, France) into a sterile glass infusion bottle. The solution was stored at room temperature. The pH of the final solution was 5.5.

Stability Testing

Portions of the solutions were repeatedly taken as samples for analysis over a period of 2 weeks. After 2 weeks, the EM 12 was still present and retained its full biological efficacy.

Testing of Immunomodulatory Efficacy

In order to investigate the immunomodulatory efficacy of the solutions produced, human monocytes were isolated from peripheral blood mononuclear cells (PBMCs) and were activated with bacterial LPS (lipopolysaccharide). The concentration of TNF-α and IL-12 in the supernatant liquors from all cell cultures was determined by means of sandwich ELISAs (Biosource Europe, Fleurus, Belgium).

TABLE 2

The effect of an EM12 solution produced according to the above Example on the TNF-α and IL12 production of LPS-activated monocytes.

|  | Ø | | EM 12 10 μg/ml | | EM 12 2 μg/ml | |
| --- | --- | --- | --- | --- | --- | --- |
|  | pg/ml | % inh* | pg/ml | % inh* | pg/ml | % inh* |
| TNF-α | 23678 | 0 | 9548 | 61 | 9915 | 60 |
| IL-12 | 2534 | 0 | 464 | 79 | 528 | 74 |

*% inh., = % inhibition of TNF-α or IL-12 production in the control without inhibitors.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A stable aqueous solution containing 3-(1-oxo-1,3-dihydroisoindol-2-yl)-piperidine-2,6-dione (EM 12) for parenteral administration, said solution comprising EM 12 dissolved in an isotonic glucose solution, and said stable aqueous solution having a pH less than or equal to 5.5.

2. A stable aqueous solution according to claim 1, wherein said solution has a 3-(1-oxo-1,3-dihydroisoindol-2-yl)-piperidine-2,6-dione content of at least 0.2 mg/ml.

3. A method of producing a stable aqueous solution containing 3-(1-oxo-1,3-dihydroisoindol-2-yl)-piperidine-2, 6-dione (EM 12), said method comprising:

adding EM 12 to an isotonic glucose solution with a pH of 4 to 5;

shaking the resulting mixture until the added EM 12 is substantially completely dissolved, and filtering the resulting solution under aseptic conditions.

4. A method according to claim 3, further comprising treating the resulting mixture with ultrasound in order to assist dissolution of the EM 12.

* * * * *